United States Patent [19]
Wirtz et al.

[11] Patent Number: 5,939,089
[45] Date of Patent: Aug. 17, 1999

[54] METHOD FOR PROVIDING A STABLE PROTECTIVE COATING FOR UV SENSITIVE PESTICIDES

[75] Inventors: Kevin R. Wirtz, Mosinee; Stuart E. Lebo, Schofield; Michael E. Sanford, Wausau, all of Wis.

[73] Assignee: LignoTech USA, Inc., Rothschild, Wis.

[21] Appl. No.: 09/057,877

[22] Filed: Apr. 9, 1998

[51] Int. Cl.[6] ................................................. A01N 25/28
[52] U.S. Cl. ..................... 424/418; 424/408; 424/417; 424/419; 424/493; 424/195.1; 424/93.46; 530/500; 427/213.3; 427/213.36
[58] Field of Search ...................... 424/405, 408, 424/417, 418, 419, 493, 93.46, 93.48, 195.1; 530/500, 507; 427/213.3, 213.36

[56] References Cited

U.S. PATENT DOCUMENTS

| | | | |
|---|---|---|---|
| 5,292,533 | 3/1994 | McMahon et al. | 424/408 |
| 5,552,149 | 9/1996 | Lebo, Jr. et al. | 424/408 |
| 5,608,040 | 3/1997 | Hüttermann et al. | 530/500 |
| 5,720,792 | 2/1998 | Fischer et al. | 71/11 |

*Primary Examiner*—Neil S. Levy
*Attorney, Agent, or Firm*—Andrus, Sceales, Starke & Sawall

[57] ABSTRACT

A method of encapsulating a pesticide with an ultraviolet protectant comprises the steps of forming a slurry of a pesticide and a lignin-containing material, and spraying a stream of acid and the slurry into contact with one another to precipitate the lignin-containing material onto the pesticide and form a protective coating on the pesticide. The pesticide is preferably a biopesticide, and the lignin-containing material is preferably kraft lignin. The method is easily adapted to industrial processes currently used for pesticide production by simply changing the spray drier from a single nozzle system to a dual spray nozzle and then adding the acid stream to the dual nozzle.

17 Claims, 1 Drawing Sheet

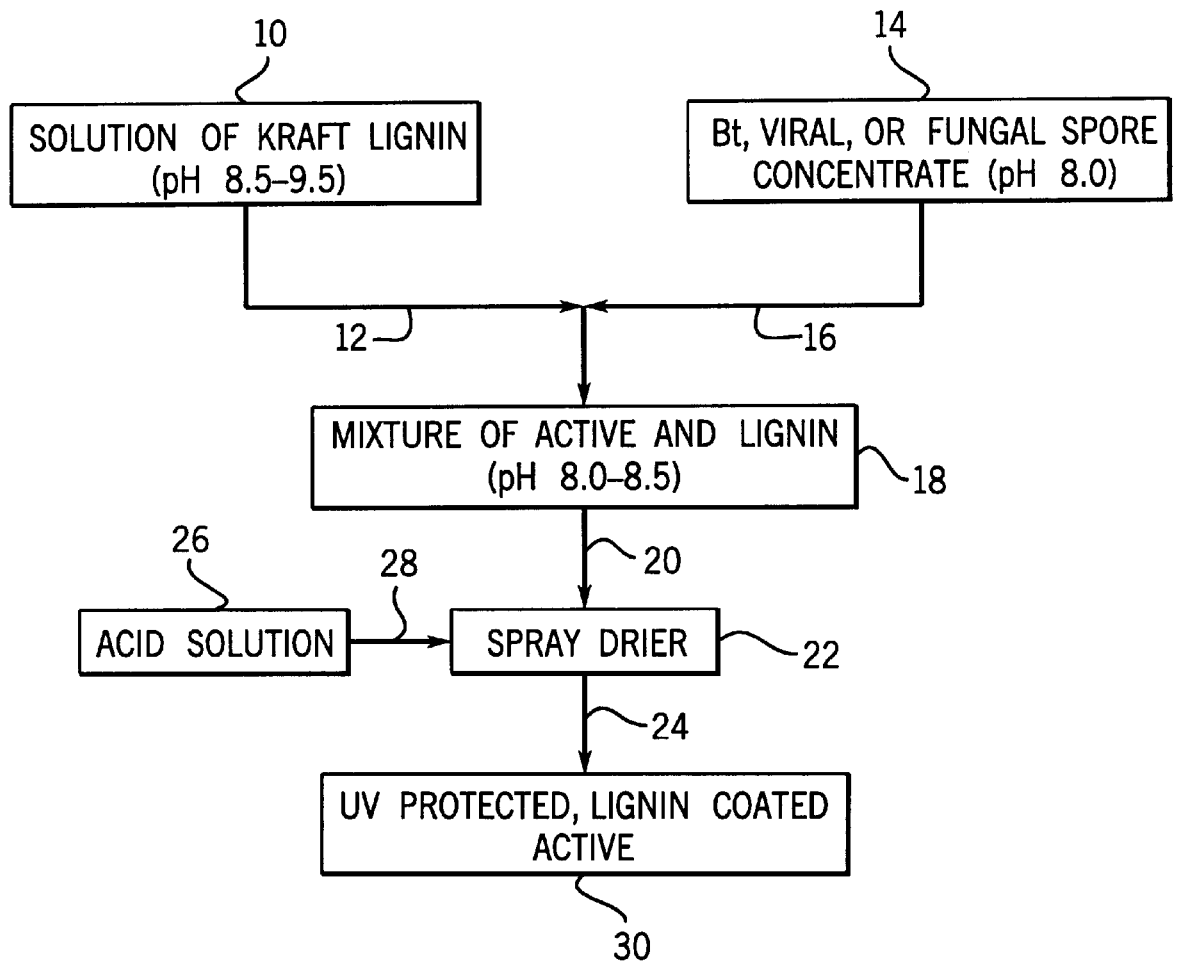

```
    10                                    14
┌─────────────────────┐         ┌──────────────────────────┐
│ SOLUTION OF KRAFT   │         │ Bt, VIRAL, OR FUNGAL SPORE│
│ LIGNIN (pH 8.5-9.5) │         │ CONCENTRATE (pH 8.0)     │
└─────────────────────┘         └──────────────────────────┘
         │ 12                              │ 16
         └──────────────┬──────────────────┘
                        ▼
            ┌─────────────────────────────┐
            │ MIXTURE OF ACTIVE AND LIGNIN│─18
            │      (pH 8.0-8.5)           │
            └─────────────────────────────┘
                        │ 20
   26          28       ▼
┌──────────┐     ┌───────────────┐
│   ACID   │────▶│  SPRAY DRIER  │─22
│ SOLUTION │     └───────────────┘
└──────────┘             │ 24
                         ▼
            ┌─────────────────────────────┐
            │ UV PROTECTED, LIGNIN COATED │
            │           ACTIVE            │
            └─────────────────────────────┘
                         30
```

FIG. 2

METHOD FOR PROVIDING A STABLE PROTECTIVE COATING FOR UV SENSITIVE PESTICIDES

CROSS-REFERENCE TO RELATED APPLICATIONS

STATEMENT REGARDING FEDERALLY SPONSORED RESEARCH OR DEVELOPMENT

BACKGROUND OF THE INVENTION

The present invention relates to pesticides, and more particularly, to a method of providing a stable protective coating for UV sensitive pesticides.

The design of pesticides which do not accumulate in the environment has led to products with limited life and efficacy in the field due to solar UV sensitivity. These biopesticide materials consist of bacteria, nuclear polyhedrosis viruses, nematodes, and fungal spores. The short residual activity of biopesticides due to sunlight-induced UV degradation within hours of application decreases the usefulness and market impact that these products can have in selectively eliminating primary pests while maintaining beneficial secondary predator insects. Formulation of UV sensitive pesticides which do not have a rapid knockdown of pests prior to their degradation requires the addition of a UV protectant to extend their lifetime and efficacy.

Several methods have been tried to coat or encapsulate pesticides in order to protect them from adverse effects of the environment. While UV protection is a primary concern, control of the environment around biopesticides is also required since degradation from protein hydrolysis or activation of the pesticide is a function of pH and is further influenced by the presence of water, surfactants, and other additives which might be present during application of the agent. Furthermore, during the coating or protecting of biopesticides, process conditions must not degrade the pesticide by subjecting it to adverse solvents or reagents. The coating must not interfere with the bioavailability of the pesticide through either impalatibility or undigestibility. The coating must resist dissolving off of the biopesticide either during mixing or storage in a sprayable slurry formulation, or under rainfall conditions when applied as a powder.

Early methods of protecting pesticides utilized encapsulation techniques relying upon a two phase system consisting of an emulsified oil active and an aqueous polymer phase which would polymerize at the interface to create an insoluble coating. These methods, such as described in U.S. Pat. Nos. 4,056,610, 4,497,793, and 4,557,755, are multistep processes that require special equipment, use relatively expensive polymers and solvents, and are usually not amenable to biodegradable capsules. They are not useful in the preparation of biopesticide formulations due to the absence of an emulsion interface or lack of applicability to solid particles. Bohm et al (U.S. Pat. Nos. 4,948,586, and 4,844, 896) extended this chemistry to biopesticides, but the method required multiple mixing and emulsifying steps; multiple reagents such as emulsifiers, glidants, crosslinkers, etc.; and organic solvents. Also, the product cannot be dried prior to application due to tackiness from residual high boiling solvents used in the preparation.

Improvements to the polymerization methods were made by using natural and biodegradable polymers. Lebo, et al (U.S. Pat. No. 5,552,149) demonstrates encapsulation by crosslinking a complex formed from lignosulfonates and proteins (such as high bloom gelatin). The benefit of UV protection from the lignosulfonate is demonstrated, and the disclosure extends to biopesticides. Moss in PCT/US92/03727 encapsulates Bt and other pesticides into a base of kraft lignin, polyethylene glycol (or acetone), and water by making a water-based emulsion in oil which is precipitated from the oil with acid. Although these two methods simplify previous encapsulations by eliminating complex polymerization and special equipment, the resulting products are not easily dried to give workable powders of well-controlled particle size when applied to biopesticides. Capsules made via the Moss method also contain solvent which may cause degradation of the biopesticide over time.

Polymerization of a gel matrix in the presence of a biopesticide leads to a solution of agents entrapped into a protective matrix. Shasha et al (U.S. Pat. No. 4,344,857) uses polyhydroxy xanthate copolymerization to generate a gel in the presence of a pesticide. This insoluble, pesticide-containing matrix is then filtered and granulated. Further drying leads to a friable solid which decomposes upon rewetting. If water stability is needed, crosslinking or hardening agents are required. The conditions for formation of the matrix are rather corrosive ($H_2O_2$, $FeCl_3$, $FeSO_4$, or $NaNO_2$; and strong acid to pH as low as pH 2.0) and reaction with the pesticide is not excluded. Spence et al (U.S. Pat. No. 4,223,007) uses sacrificial amounts of RNA or protein matter to form a matrix around biopesticides via precipitation of the protein into a gel, then breaking up the gel into microbeads, then crosslinking the gel for stability. Microbead wall thicknesses of 40 to 200 microns are used to increase microbial lifetime by 40%. Nelson et al (U.S. Pat. No. 4,753,799) utilizes alginates to form hydrogel capsules with the use of calcium chloride as a complexing or crosslinking agent which toughens the outer surface of the capsules. The 0.4 to 5 mm capsules are used in a slurry to preserve nematodes in a hydrated environment. Attractants can also be incorporated into the capsule. The slurry is sprayed into the environment and the capsule regulates the loss of water over time to extend the efficacy of the nematodes. Although these gel matrix procedures simplify the earlier encapsulation techniques, the resulting materials by nature do not provide materials that can be easily stored in a dry state and resuspended at a later time.

Dimitri (U.S. Pat. No. 3,929,453 and Re. 29,238) simplifies the process of entrapping biological actives into a matrix by forming coprecipitation-inclusion composites from a mixture of kraft lignin and the pesticide. The lignin provides a protective coating and acts as a UV protectant against sunlight induced degradation. The composites are rain fast and inhibit the action of microorganisms, yet regulate the release of the active either by diffusion through the lignin matrix or by degradation or alkali dissolution of the matrix. A solution of alkali lignin salt is mixed with the biological active and emulsified. The lignin is then solidified by coprecipitation-inclusion from the alkaline solution by acidification. The product is then isolated from the co-solvent and the remaining water removed by evaporation. The matrices obtained are solids varying in dimension from 0.5 to droplet size with active to lignin ratios of 0.1:1 to 10:1.

Lebo (U.S. Pat. No. 5,529,772) improves upon the Dimitri and Spense inventions in the case of protecting biopesticides by utilizing the ability of lignosulfonates to complex with proteins. The active protein toxin in the biopesticide is reacted with the lignosulfonate to form a stable complex having the UV protecting lignin as an integral part of its structure. This is done by mixing the lignosulfonate with the biopesticide and acidifying the mixture to below the isoelectric point of the complex where the complex becomes an insoluble precipitate. The precipitate can be used as a slurry or can be isolated and dried to a powder. This procedure also improves upon the use of lignin as an adjuvant as in Hobbs (PTO/US95/01760). The UV protectant is integrally incorporated on the surface of the pesticide where it is most effective, rather than simply added to a pesticide formulation where dilution can decrease the effectiveness of the UV protectant. The pesticide is then released from the lignin in the caustic insect gut upon ingestion of the complex by the host insect.

The technology for providing UV protection to biopesticides has moved from the complex microencapsulation techniques used for chemical pesticides to the simpler coacervation methodologies, yet these methods are not prevalent in the market today. Accordingly, there remains a need for an improved process for providing UV protection to pesticides.

SUMMARY OF THE INVENTION

It is the object of this invention to provide a method of protecting pesticides which will easily fit into current processes for producing pesticides. Furthermore, an object is to provide a UV protective coating which will not interfere with the drying process inherently part of the production of pesticides, and which will remain on the pesticide even after redispersing the material into tank mixes from which they are applied, or after application of the pesticide as a powder.

Still another objective of this invention is to minimize the ingredients and cost of protecting pesticides using the advantages that are evident from the following description of the invention.

Accordingly, the present invention provides a method of encapsulating a pesticide with an ultraviolet protectant, comprising the steps of forming a slurry of a pesticide and a lignin-containing material; and spraying a stream of acid and said slurry into contact with one another to precipitate the lignin-containing material onto the pesticide and form a protective coating on said pesticide. The pesticide is preferably a biopesticide and the lignin-containing material is preferably kraft lignin. The acid may be a mineral acid or an organic acid such as formic, sulfuric or acetic acid.

This invention is applicable to any biopesticide, and without the use of acid, significant loss of coating would occur from subsequent dissolution or exposure to rain. The use of acid in a dual nozzle system provides effective UV protection. Sulfuric acid is demonstrated to be much more effective in controlling the product pH level since formic acid tends to volatilize in the process. Changing the proportions of lignin in the formulation is a means of controlling the thickness of the protective UV coating and, in the case of finely divided biopesticides such as npv's, may be a means for controlling the number of inclusion bodies or amount of actives in each powder particle. The higher coating levels remain on the particle and are not dissolved into solution to any significant degree. Process variations contributing to a decrease in acid may lead to slightly higher solution pH and a slight increase in dissolved coating, but in spite of variations in acid levels, the amount of UV protective coating retained is substantial. A bioassay of Bt produced by this method shows that biopesticides can be effectively coated with UV protectant without detriment to the biopesticide. The coating provided is stable and not diluted into solution, remaining on the particle where it is most effective at providing UV protection. The method itself is easily adapted to industrial processes currently used for biopesticide production. By adding the UV protecting lignin to the biopesticide slurry, and by changing the spray drier from a single nozzle system to a dual spray nozzle, then adding an acid stream to the drier through the dual nozzle, one can simply obtain a biopesticide with a stable UV protective coating without having to add significant steps and processing equipment to a biopesticide production line.

BRIEF DESCRIPTION OF THE SEVERAL VIEWS OF THE DRAWING

In the drawings:

FIG. 1 is a schematic diagram of the coating process for encapsulating a pesticide in accordance with the present invention; and FIG. 2 is a schematic perspective view of a dual spray nozzle used in the process of FIG. 1.

DETAILED DESCRIPTION OF THE INVENTION

It has been found that the UV sensitivity of agricultural pesticides including chemical toxins and biological pesticides can be greatly reduced by encapsulation according to this invention. Such pesticides include any UV sensitive pesticide whether that pesticide is a synthetic or natural chemical toxin, or a biopesticide, i.e. a biologically derived pesticide. As used herein the term "pesticide" has its normal connotation, and is intended to encompass insecticides, herbicides, fungicides, rodenticides, molluscicides, miticides, ovicides, algicides, larvacides, bactericides, and nematocides.

Efforts in the pesticide industry to produce non-transgenic biopesticides has provided four major classes of biopesticides: bacterium (e.g. *Bacillus thuringiensis, Bacillus sphaericus, Bacillus popilliae, Bacillus cereus, Pseudomonas fluorescens, Serratia marcscens, Escherichia coli*, etc.), nuclear polyhedrosis viruses (e.g. *Heliothis zea, H. virescens, Lymantria dispar, Orgyia pseudotsugata, Neodiprion sertifer, Autographa californica*, etc.), hereinafter also referred to as "npv's," nematodes (e.g. *Neoaplectana carpocapsae, Octomyomermis muspratti, Steinernema carpocapsae, Romanomermis culicivora*, etc.), and fungal spores (e.g. *Verticittum lecanii*, Entomophthora genus, etc.). These products are grown either from cultured media such as batch cell broth production or in spawning media, or, in cases of npv's, from growth in a host insect body. In most cases, such as for Bt's and npv's, the biopesticides are obtained as finely divided particulates in a paste or slurry form. From this point, the biological actives are treated with preservatives and any additives which go into the final formulation. The materials are then granulated and dried for use in the end applications. Spray drying is a well established method for the final processing of these products. Bt endotoxins, spores, and npv's are well suited for this method of processing since they can withstand the short exposure time of heat in a spray drier required to reduce the moisture content of the formulation to less than five percent of the total formulated weight. The lower moisture levels are desirable for the long term storage of these products.

The overall production of these biopesticides is time consuming and expensive. Once the material is collected in post production, it is undesirable to send the biopesticides through several more steps of processing in order to complete the formulation, especially, steps that might increase the manufacturing costs and decrease the pesticidal activity of the products.

Chemical toxins include but are not limited to pyrethrum, a naturally derived insecticide; pyrethroids, i.e. synthetic copies of pyrethrum, such as allethrin, cyfluthrin, cypermethrin, fenothrin, flucythrinate or indothrin; and organophosphates, such as crufomate, dursban, dicrotophos, parathion or phorate. Chemical toxins usable in the method of the present invention are insoluble in water, stable to mildly basic and acidic hydrolysis conditions, typically have a melting point above about 110° C. and are UV sensitive. The list of such toxins (by trade name) includes (1) pesticides: Amitraz, Azinophos-methyl, Cyfluthrin, Flufenoxuron, Resmethrin, (2) fungicides: Hexconazole, Captafol, Captan, Carbendazim, Carbofuran, Folpet; and (3) herbicides: Diuron, Simazine.

The invention provides a simple, but very effective in-process method for producing a UV protective coating for biopesticides and/or chemical pesticides. In this method, a mixture 18 of biopesticide and/or chemical pesticide and kraft lignin is made such that the final pH of the mixture 18 is above the precipitation pH of the lignin, i.e. pH 8.0–8.5 but typically pH 8.2. This can be accomplished, for example, by adding a solution 10 of kraft lignin at a pH of between 7.0 to 12.0 but preferably 8.5 to 9.5 via line 12 to a slurry 14 of biopesticide at pH 8.0 (screened to a size compatible with the spray nozzle as will hereinafter be described) added via line 16. The amount of kraft lignin added to the solution varies from a solids ratio of 1:10 to as much as 10:1 parts lignin solids to biopesticide solids, respectively, but more preferably from 1:10 to 2:1 parts lignin to biopesticide solids. Other lignins which are soluble at pH 7.0–12.0 and insoluble at lower pH are acceptable, such as organosolve lignin. Although the kraft lignin is a UV protectant in itself and will provide the UV protective coating, other auxiliary UV protectants may also optionally be added to the kraft lignin. Oxylignins and humates may be added to the kraft lignin in as much as 30% level to increase the UV absorbing characteristics of the coating. These materials are particularly attractive since they are soluble in the kraft lignin solution and also are insoluble at lower pH. Other chemical UV protectants can be added at this time and will be incorporated at levels dependent upon their compatibility to the system. In addition, other water soluble polymers, such as lignosulfonates, can be added at this point to cause slow release of the biopesticides by modifying the degree of insolubility of the kraft lignin addition, and total solids of 6–10% are not unusual for drier feed. The resulting mixture may have other formulation ingredients added either prior to the lignin addition or afterward.

Any lignosulfonate, sulfonated lignite, sulfonated tannin or related water soluble compound such as naphthalene sulfonates or condensed naphthalene sulfonates can be used to modify the degree of insolubility of the kraft lignin coating which functions as a UV protectant in the invention. These compounds are well known and are derived from the sulfite pulping of wood, by sulfonation of lignins derived from the kraft pulping of wood, by sulfonation of tannins derived from wood barks, etc. The water soluble lignin materials used are typically in the salt form (i.e. sodium, calcium, potassium, etc.). Preferable materials are those with high molecular weight, strong absorptivities in the 290–400 nm wavelength range and sufficient sulfonation to ensure water solubility.

The lignosulfonates which may be utilized are the treated or untreated spent sulfite liquors containing the desired effluent lignosulfonate solids obtained from wood conversion as the sulfite waste pulping liquor. These, as indicated, may be utilized in the "as is" or whole liquor condition. They may also be utilized as a purified lignosulfonate material from, or in which the sugars and other saccharide constituents have been removed and/or destroyed, or additionally inorganic constituents have been partially or fully eliminated. Also, as noted above, sulfonated or sulfoalkylated kraft lignin can be used to modify the degree of insolubility of the kraft lignin coating.

As used herein, the term "kraft lignin" has its normal connotation, and refers to the substance which is typically recovered from alkaline pulping black liquors such as are produced in the kraft, soda and other well known alkaline pulping operations. The kraft lignin may be utilized in its "as is" or whole lignin condition, but may also be utilized as a purified material. The term "sulfonated lignin", as used in the specification refers to the product which is obtained by the introduction of sulfonic acid groups into the kraft lignin molecule, as may be accomplished by reaction of the kraft lignin with sulfite or bisulfite compounds, so that kraft lignin is rendered soluble in water. As used herein, the term "sulfite lignin" refers to the reaction product of lignin which is inherently obtained during the sulfite pulping of wood, and is a principle constituent of spent sulfite liquor. The term "lignosulfonate" ($LSO_3$) encompasses not only the sulfite lignin, but also the sulfonated lignin herein above described. Any type of lignosulfonate that is hardwood, softwood, crude, or pure may be employed, and as noted previously, lignosulfonates may be utilized in their as is or whole liquor condition. For example calcium lignosulfonates, sodium lignosulfonates, ammonium lignosulfonates, modified lignosulfonates and mixtures or blends thereof may be utilized herein. Lignosulfonates are available from numerous sources in either aqueous solution or dried powder forms. For example Lignotech USA, Inc. sells lignosulfonates under the trade designations Lignosol, Norlig, and Marasperse which are appropriate for use in the present invention.

As noted previously, naphthalene sulfonates or condensed naphthalene sulfonates may also be used to modify solubility. Naphthalene sulfonates are well known, and are typically synthesized via sulfonation of naphthalene, and naphthalene condensates.

For convenience, the following description refers only to processing a biopesticide and lignin mixture. However, the process described applies equally to a chemical pesticide and lignin mixture.

The mixture 18 of lignin and biopesticide (and/or chemical pesticide) is then fed via line 20 to the spray drier 22 which has been modified so that the spray nozzle is a dual spray nozzle similar in function to a Spraying Systems Co. Nozzle 1/8VAU-SS+SUV67-SS. The mixture 18 of lignin and biopesticide (and/or chemical pesticide) is atomized, represented by line 24, with said atomized stream 24 passing through a stream 28 of acid solution 26. The acid mixes into the lignin-biopesticide (and/or chemical pesticide) stream, causing the lignin to precipitate and form a UV protected lignin coated pesticide 30. The flow rates and concentrations are set so that the atomization is efficient and so that the acid is present in a sufficient quantity to precipitate the kraft lignin onto the biopesticide (and/or chemical pesticide) and form a coating on the biopesticide (and/or chemical pesticide). The resulting dry particles have a pH in the range of pH 4.0 to 6.0. These acid concentrations and flow rates allow the resulting dry powder to be slurried in the process water of a farmer's tank mix and maintain a final pH of the biopesticide mix below 8.5, i.e. the precipitation pH of the lignin. The purpose of this dual spray nozzle is to send an atomized stream of lignin-containing biopesticide (and/or chemical pesticide) mixture through a second stream of acid at a controlled rate. These combined streams are atomized at a rate sufficient to produce a desirable particle size. The typical average particle size obtained is around 10 microns, with a typical range distribution of ±30 microns depending on the nature of biopesticide particles.

Referring to FIG. 2, there is schematically shown a dual spray nozzle representative of drier 22 for accomplishing the encapsulation steps described above. As illustrated, nozzle 22 has three inlets and three outlets. One inlet 32 accepts air under pressure for atomizing the mixture 18 of pesticide and lignin. A second inlet 34 accepts the mixture 18 to be atomized, and the third inlet 36 accepts acid solution 26. Central outlet 38 provides an exit for the atomizing air and mixture 18 while opposite side outlets 40 and 42 direct the acid solution 26 inwardly at the mixture 18 exiting nozzle 22 from central outlet 38. Thus, an atomized stream 44 of lignin and pesticide mixture 18 is passed through streams 46 and 48 of acid resulting in a coated pesticide represented by atomized stream 50. The final pH of the coated particles should be between a pH of 3–8, but preferably 4–6.

The concentrations of lignin, biopesticide (and/or chemical pesticide), and additives determine the number of active bodies in each particle. The atomization and dimensions of the drier determine the size of each particle, and the inlet and outlet temperatures determine the moisture content of the resulting UV protected and coated biopesticide (and/or chemical pesticide). Typical inlet temperatures of 200° C. to 250° C. and outlet temperatures of 60° C. to 100° C. are used for npv's and Bt's without significant degradation to the product. More specifically, an inlet temperature of 230° C. and an outlet temperature of 75–90° C. is preferably used. The air pressure on the atomizer is typically 40 psi, but can be varied to maintain efficient atomization.

Preparations were made according to the examples listed below using Bt slurry. Kaolin clay was used to demonstrate the generality of the application. Kaolin clay was included to establish a baseline because the Bt slurry obtained already contained a small amount of UV protectant. The acid was varied between formic acid and sulfuric acid, which are the preferred acids for contact with biological agents, but any compatible organic acid (preferably formic, or acetic) or mineral acid can be employed. Formic acid volatilizes in the spray drier, requiring a higher loading on Bt solids than sulfuric acid. Examples of acceptable organic acids include formic, acetic, propionic, oxalic, gluconic, malonic, and succinic acids. Examples of acceptable mineral acids are hydrochloric, sulfuric, phosphoric, sulfurous, or phosphorous acids.

The resulting coated powders were tested for stability of the coating. UV spectroscopy was used to quantitatively determine the amount of coating and/or added UV protectant that dissolved off of the Bt or Kaolin clay particle when added to water at a pH of 8.1. When using 30% by weight of protective coating (10 parts additional protectant—an oxylignin—was added to 90 parts of kraft lignin), only 3.5% of the total coating and/or UV protectant was soluble in solution (Examples 1 and 3). When increasing this loading to 50% of protective coating, only 8.8% of the total protective coating dissolved into the water (Example 6). The difference may be attributed partly to the difference in pH between the two dry powders. When acid was not used in the spray drying process, 95% of the coating dissolved off of the Bt at 30% by weight of coating.

EXAMPLE 1

Preferred Embodiment of the Invention Using Formic Acid

A slurry of Bt toxin was diluted to 8% solids and screened through an 80 mesh sieve, then adjusted to pH 8.0 with a 2% solution of sodium hydroxide. A solution of 9 parts of kraft lignin (Curan 100 from LignoTech USA) and 1 part of oxylignin (Vanisperse A from LignoTech USA) was dissolved into water and adjusted to pH 8.2 and 8% solids. An amount of slurry equivalent to 70 parts of Bt solids was mixed with 30 parts of solids of the kraft lignin solution. The resulting mixture was fed through the central atomizing nozzle of the Spraying Systems Co. Nozzle 1/8VAU-SS+ SUV67-SS at a flow rate of 45 ml/min as metered with a peristaltic pump. A 2% solution of formic acid was metered through the fan-air port at 30 ml per minute. This is equivalent to 15% formic acid on total solids. The spray drier employed is a Bowen Engineering, Inc., Laboratory Spray-Aire Model. The inlet temperature was maintained at 230° C. and the outlet temperature was maintained at 75° C. The resulting powder had an average particle size of 7.6 microns. The powder was quantitatively dissolved in water of pH 8.1 to give a suspension of coated Bt at pH 4.9. After agitating for an hour, the amount of coating which dissolved into solution was determined to be 3.4% of the theoretical weight of coating present by UV spectroscopy. A 95% bioassay was obtained in comparison to the starting material. This Example shows that the Bt is effectively coated with UV protectant. The coating is stable in solution, remaining on the particle where it is most effective, and not diluted into solution. Furthermore, the processing conditions are not detrimental to the efficacy of the Bt.

EXAMPLE 2

Demonstration of the Effect of Acid

Example 1 was repeated without the use of formic acid through the fan air inlet. A powder with an average particle size of 15.1 microns was obtained. This dissolved into pH 8.1 water to give a final solution pH of 8.7. After 1 hour of agitation the amount of coating which dissolved into solution was determined to be 95.2% of the theoretical weight of coating present. This significant loss shows that the use of acid in a dual nozzle system is both effective and necessary for effective UV protection.

EXAMPLE 3

Demonstration of Variations in the Amount of Acid

A slurry of Bt toxin was diluted to 8% solids and screened through an 80 mesh sieve, then adjusted to pH 8.0 with a 2% solution of sodium hydroxide. A solution of kraft lignin (Curan 100 from LignoTech USA) was dissolved into water and adjusted to pH 8.2 and 8% solids. An amount of slurry equivalent to 84 parts of Bt solids was mixed with 16 parts of solids of the kraft lignin solution. The resulting mixture was fed through the central atomizing nozzle at a flow rate of 45 ml/min as metered with a peristaltic pump. A 1.3% solution of formic acid was metered through the fan-air port at 30 ml per minute. This is equivalent to 10% formic acid on total solids. The inlet temperature was maintained at 230° C. and the outlet temperature was maintained at 75° C. The resulting powder had an average particle size of 11.8 microns. The powder was quantitatively dissolved in water of pH 8.1 to give a suspension of coated Bt at pH 5.7. After agitating for an hour, the amount of coating which dissolved into solution was determined to be 6.9% of the theoretical weight of coating present by UV spectroscopy. The decrease in acid as compared to Example 1 led to a higher solution pH and a slight increase in lost coating. However, in spite of the variation in acid, the amount of UV protective coating retained is substantial.

EXAMPLE 4
Preferred Embodiment of the Invention for Other Particulates and Acids In order to establish generality of the method and establish a baseline for performance, Bt was replaced in the procedure for Example 1 by kaolin clay, and formic acid was replaced by sulfuric acid. Due to lack of volatilization of the sulfuric acid, the concentration of sulfuric was reduced to 0.5% and the flow rate increased to 40 ml per minute (⅓ the amount of formic acid addition). This is equivalent to 5% sulfuric acid on total solids. The addition rate of 45 ml/min was maintained for the kaolin mixture. All other parameters were held constant with Example 1. The resulting powder had an average particle size of 8.4 microns. The powder was quantitatively dissolved in water of pH 8.1 to give a suspension of coated Bt at pH 3.9. After agitating for an hour, the amount of coating which dissolved into solution was determined to be 4.1% of the theoretical weight of coating present. This result demonstrates that the method should be applicable to any biopesticide particulates and shows that sulfuric acid is effective in controlling the product pH level.

EXAMPLE 5
Repeat of Example 2 Demonstration on Kaolin Clay

Example 4 was repeated with the exception of the use of acid. The resulting powder had an average particle size of 3.3 microns. The powder was quantitatively dissolved in water of pH 8.1 to give a suspension of coated Bt at pH 8.7. After agitating for an hour, the amount of coating which dissolved into solution was determined to be 96.2% of the theoretical weight of coating present. This significant loss verifies that the use of acid in the dual nozzle system is both effective and necessary for effective UV protection, and that the effect is not dependent upon substrate, but on the use of acid.

EXAMPLE 6
Effect of Loading of Lignin on Actives

The amount of coating phase was increased to 50% of the total solids in order to demonstrate the integrity of the coating. A slurry of kaolin clay was diluted to 8% solids, then adjusted to pH 8.0 with a 2% solution of sodium hydroxide. A solution of 9 parts of kraft lignin (Curan 100 from LignoTech USA) and 1 part of oxylignin (Vanisperse A from LignoTech USA) was dissolved into water and adjusted to pH 8.2 and 8% solids. An amount of slurry equivalent to 70 parts of kaolin solids was mixed with 30 parts of solids of the kraft lignin solution. The resulting mixture was fed through the central atomizing nozzle of the Spraying Systems Co. Nozzle 1/8/VAU-SS at a flow rate of 45 ml/min as metered with a peristaltic pump. A 2% solution of formic acid was metered through the fan-air port at 30 ml per minute, being equivalent to 15% formic acid on total solids. The spray drier conditions were maintained as in the other Examples. The powder was quantitatively dissolved in water of pH 8.1 to give a suspension of coated kaolin at pH 5.3. After agitating for an hour, the amount of coating which dissolved into solution was determined to be 8.8% of the theoretical weight of coating present by UV spectroscopy. This Example shows that the higher coating levels remain on the particle and are not dissolved into solution to any significant level. Changing the proportions of lignin in the formulation is a means of controlling the thickness of the protective UV coating and, in the case of fine divided biopesticides such as npv's, may be a means for controlling the number of inclusion bodies or amount of actives in each powder particle.

The previous Examples demonstrate that this invention is applicable to any biopesticide. The Examples demonstrate that without the use of acid, significant loss of coating would occur from subsequent dissolution or exposure to rain. The use of acid in the dual nozzle system is both effective and necessary for effective UV protection. Sulfuric acid is demonstrated to be much more effective in controlling the product pH level since the formic acid tends to volatilize in the process. Changing the proportions of lignin in the formulation is a means of controlling the thickness of the protective UV coating and, in the case of finely divided biopesticides such as npv's, may be a means for controlling the number of inclusion bodies or amount of actives in each powder particle. The higher coating levels remain on the particle and are not dissolved into solution to any significant degree. Process variations contributing to a decrease in acid may lead to a slightly higher solution pH and a slight increase in dissolved coating, but in spite of variations in acid levels, the amount of UV protective coating retained is substantial. A high bioassay of Bt produced by this method shows that the biopesticides can be effectively coated with UV protectant without detriment to the biopesticide. The coating provided is stable and not diluted into solution, remaining on the particle where it is most effective at providing UV protection. The method itself is easily adapted to industrial processes currently used for biopesticide production. By adding the UV protecting lignin to the biopesticide slurry, and by changing the spray drier from a single nozzle system to the described type of dual spray nozzle, then adding an acid stream to the drier through the dual nozzle, one can simply obtain a biopesticide with a stable UV protective coating without having to add significant steps and processing equipment to a biopesticide production line.

We claim:

1. A method of encapsulating a pesticide with an ultraviolet protectant, comprising the steps of:
   forming a slurry containing a mixture of a pesticide and a lignin-containing material;
   spraying said slurry to form an atomized stream of said mixture; and
   spraying a stream of acid into contact with the atomized stream of said mixture to precipitate the lignin-containing material onto the pesticide and form a protective coating on said pesticide.

2. The method of claim 1 wherein the step of spraying said acid comprises atomizing said acid.

3. The method of claim 1 wherein the step of forming said slurry comprises mixing a lignin-containing material in solid form with a pesticide slurry.

4. The method of claim 1 further comprising the step of controlling the rate of spraying of said stream of acid and said slurry to produce a protected particle of a desired size.

5. The method of claim 1 wherein said pesticide is a biopesticide.

6. The method of claim 1 wherein said pesticide is a chemical toxin.

7. The method of claim 1 wherein said acid is a mineral acid selected from the group consisting of hydrochloric, sulfuric, sulfurous, phosphoric, and phosphorous acids.

8. The method of claim 1 wherein said acid is an organic acid selected from the group consisting of formic, acetic, gluconic, malonic, oxalic, propionic, and succinic acids.

9. The method of claim 1 wherein said lignin-containing material is a lignin soluble in water at a pH of between about 7 to 12 and insoluble at lower pH.

10. The method of claim 9 wherein said lignin-containing material is a kraft lignin.

11. The method of claim 1 wherein said lignin-containing material is organosolve lignin.

12. The method of claim 1 wherein said slurry contains a solids ratio of from about 1:10 to about 10:1 parts lignin solids to pesticide solids.

13. The method of claim 1 further including the step of adding an auxiliary UV protectant to said slurry to modify the degree of UV protection provided by the protective coating.

14. The method of claim 13 wherein said auxiliary UV protectant is selected from the group consisting of oxylignins and humates.

15. The method of claim 13 wherein said auxiliary UV protectant is added in as much as about 30% by weight.

16. The method of claim 1 further including the step of adding a water soluble agent to said slurry to modify the degree of water insolubility of the protective coating.

17. The method of claim 16 wherein said water soluble agent is selected from the group consisting of lignosulfonate, sulfonated lignite, sulfonated tannin, a naphthalene sulfonate, a condensed naphthalene sulfonate and mixtures thereof.

* * * * *